(12) United States Patent
Lappin et al.

(10) Patent No.: US 10,390,970 B2
(45) Date of Patent: Aug. 27, 2019

(54) ORTHOPAEDIC SURGICAL SAW ASSEMBLY FOR REMOVING AN IMPLANTED GLENOID COMPONENT AND METHOD OF USING THE SAME

(71) Applicant: DEPUY SYNTHES PRODUCTS, INC., Raynham, MA (US)

(72) Inventors: Kyle E. Lappin, Fort Wayne, IN (US); Jason M. Chavarria, Warsaw, IN (US); Patrick G. McElhaney, Jr., Juniper, FL (US); David M. Warlop, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 535 days.

(21) Appl. No.: 14/231,027

(22) Filed: Mar. 31, 2014

(65) Prior Publication Data

US 2014/0214041 A1    Jul. 31, 2014

Related U.S. Application Data

(62) Division of application No. 13/371,979, filed on Feb. 13, 2012, now Pat. No. 8,696,677.

(51) Int. Cl.
  *A61B 17/14* (2006.01)
  *A61F 2/46* (2006.01)
  *A61F 2/40* (2006.01)

(52) U.S. Cl.
  CPC .......... *A61F 2/4612* (2013.01); *A61B 17/149* (2016.11); *A61F 2/4081* (2013.01)

(58) Field of Classification Search
  CPC ........................ A61B 2017/145; A61B 17/149
  See application file for complete search history.

(56) References Cited

U.S. PATENT DOCUMENTS

| 184,804 A | 11/1876 | Stohlmann |
| 4,709,699 A | 12/1987 | Michael et al. |
| 2006/0122458 A1* | 6/2006 | Bleich ................ A61B 17/1659 600/101 |
| 2008/0243249 A1 | 10/2008 | Kohm et al. |

(Continued)

FOREIGN PATENT DOCUMENTS

| JP | 2006-314367 A | 11/2006 |
| JP | 2012-525927 A | 10/2012 |

(Continued)

OTHER PUBLICATIONS

Australian Office Action, Patent Application No. 2013200534, dated Jun. 13, 2014, 3 pages.

(Continued)

*Primary Examiner* — Samuel S Hanna
(74) *Attorney, Agent, or Firm* — Barnes & Thornburg LLP

(57) ABSTRACT

A surgical instrument for removing an implanted glenoid component from the glenoid of a patient includes a protective cannula and a flexible wire saw. The flexible wire saw is positioned in the protective cannula such that both ends of the flexible wire saw extend out of one end of the protective cannula, with a portion of the middle section of the wire saw forming a loop that extends out of the other end of the protective cannula. Surgical methods for the use of such a surgical instrument are also disclosed.

4 Claims, 8 Drawing Sheets

(56) References Cited

U.S. PATENT DOCUMENTS

2010/0249938 A1    9/2010  Gunther et al.
2010/0286782 A1*  11/2010  Schaller ............ A61B 17/1642
                                                623/17.12

FOREIGN PATENT DOCUMENTS

SU        1069795 A1    1/1984
WO     2009100200 A1    8/2009

OTHER PUBLICATIONS

Tomita K et al., The Threadwire Saw: A new Device for Cutting Bone, Journal of Bone and Joint Surgery, American Volume, Journal of Bone and Joint Surgery, US, vol. 78-A, No. 12, Dec. 1, 1996, pp. 1915-1917, XP000637795, ISSN: 0021-9355.
European Search Report, European Patent Application No. 13152597.5-1654, dated Apr. 10, 2013, 7 pages.
European Search Report, European Patent Application No. 13152587.5-1654, dated Apr. 10, 2013, 7 pages.

* cited by examiner

ORTHOPAEDIC SURGICAL SAW ASSEMBLY FOR REMOVING AN IMPLANTED GLENOID COMPONENT AND METHOD OF USING THE SAME

This application claims priority to and is a divisional application of U.S. patent application Ser. No. 13/371,979, entitled "ORTHOPAEDIC SURGICAL SAW ASSEMBLY FOR REMOVING AN IMPLANTED GLENOID COMPONENT AND METHOD OF USING THE SAME," which was filed on Feb. 13, 2012 and is expressly incorporated herein by reference.

TECHNICAL FIELD

The present disclosure relates generally to an orthopaedic instrument for use in the performance of an orthopaedic joint replacement procedure, and more particularly to an orthopaedic surgical saw assembly for removing an implanted glenoid component.

BACKGROUND

During the lifetime of a patient, it may be necessary to perform a total shoulder replacement procedure on the patient as a result of, for example, disease or trauma. In a total shoulder replacement procedure, a humeral component having a prosthetic head is used to replace the natural head of the patient's humerus. The humeral component typically includes an elongated stem that is implanted into the intramedullary canal of the patient's humerus. In such a total shoulder replacement procedure, the natural glenoid surface of the scapula is resurfaced or otherwise replaced with a glenoid component that provides a bearing surface upon which the prosthetic head of the humeral component articulates.

From time-to-time, revision surgery is performed to replace a previously-implanted glenoid component. In such a revision surgery, the previously implanted glenoid component is surgically removed and a replacement glenoid component is implanted in the patient's glenoid. The subcondylar plate may be damaged or missing subsequent to revision surgery. Revision surgery may also result in defects, some of which may be fairly large, in the cancellous bone of the glenoid vault of the scapula. Fixation of a revision glenoid component can be difficult to achieve with the limited bone remaining on the glenoid vault of the scapula after the revision surgery has been performed.

SUMMARY

According to one aspect, a method of surgically removing an implanted glenoid component from the glenoid of a patient includes positioning a flexible wire saw between a medial surface of a platform of the implanted glenoid component and the glenoid of the patient. The flexible wire saw is then reciprocated so as to cut through one or more anchors extending from the medial surface of the platform of the implanted glenoid component. The platform of the implanted glenoid component is then removed from the glenoid of the patient such that the one or more cut anchors remain in the glenoid of the patient.

The method also includes operating a surgical tool so as to remove the one or more cut anchors from the glenoid of the patient subsequent to removal of the platform of the implanted glenoid component. In an embodiment, the cut anchors are drilled from the glenoid of the patient with a surgical drill.

The flexible wire saw may be initially positioned behind the superior-most edge of the implanted glenoid component and thereafter advanced inferiorly from the superior-most edge of the implanted glenoid component to the inferior-most edge of the implanted glenoid component.

The flexible wire saw may be positioned in a protective cannula such that the flexible wire saw forms a loop extending out of the cannula, with such a loop being positioned between the medial surface of the platform of the implanted glenoid component and the glenoid of the patient. In such an embodiment, the flexible wire saw is reciprocated within the protective cannula.

The protective cannula may be embodied as a dual-lumen cannula such that a first end of the flexible wire saw extends out of a first end of the first cannula, with a second end of the flexible wire saw extending out of a first end of the second cannula. The middle section of the flexible wire saw extends between a second end of the first cannula and a second end of the second cannula.

The flexible wire saw may be embodied as a Gigli saw.

The flexible wire saw may be manually reciprocated so as to cut through the one or more anchors extending from the medial surface of the platform of the implanted glenoid component. Alternatively, it may be reciprocated with a power tool.

According to another aspect, a surgical instrument for removing an implanted glenoid component from the glenoid of a patient includes a protective cannula and a flexible wire saw. The flexible wire saw is positioned in the protective cannula such that both ends of the flexible wire saw extend out of one end of the protective cannula, with a portion of the middle section of the wire saw forming a loop that extends out of the other end of the protective cannula.

The protective cannula may be embodied as a dual-lumen cannula such that a first end of the flexible wire saw extends out of a first end of the first cannula, with a second end of the flexible wire saw extending out of a first end of the second cannula. The middle section of the flexible wire saw extends between a second end of the first cannula and a second end of the second cannula.

The flexible wire saw may be embodied as a Gigli saw.

The protective cannula is metallic or polymeric.

According to another aspect, a method of surgically resecting the humeral head of a patient includes positioning a flexible wire saw in contact with the humeral head of the patient, and reciprocating the flexible wire saw so as to cut through the humeral head of the patient so as to create a substantially planar surgically prepared surface.

The flexible wire saw may initially be positioned in contact with the posterior surface of the humeral head of the patient, and thereafter advanced anteriorly so as to create a substantially planar surgically prepared surface.

The flexible wire saw may be positioned in a protective cannula such that the flexible wire saw forms a loop extending out of the cannula that is positioned in contact with the humeral head of the patient. In such an embodiment, the flexible wire saw is reciprocated within the protective cannula.

The protective cannula may be embodied as a dual-lumen cannula such that a first end of the flexible wire saw extends out of a first end of the first cannula, with a second end of the flexible wire saw extending out of a first end of the second cannula. The middle section of the flexible wire saw extends between a second end of the first cannula and a second end of the second cannula.

The flexible wire saw may be embodied as a Gigli saw positioned in contact with the humeral head of the patient.

BRIEF DESCRIPTION OF THE DRAWINGS

The detailed description particularly refers to the following figures, in which.

DETAILED DESCRIPTION OF THE DRAWINGS

Figure 1:
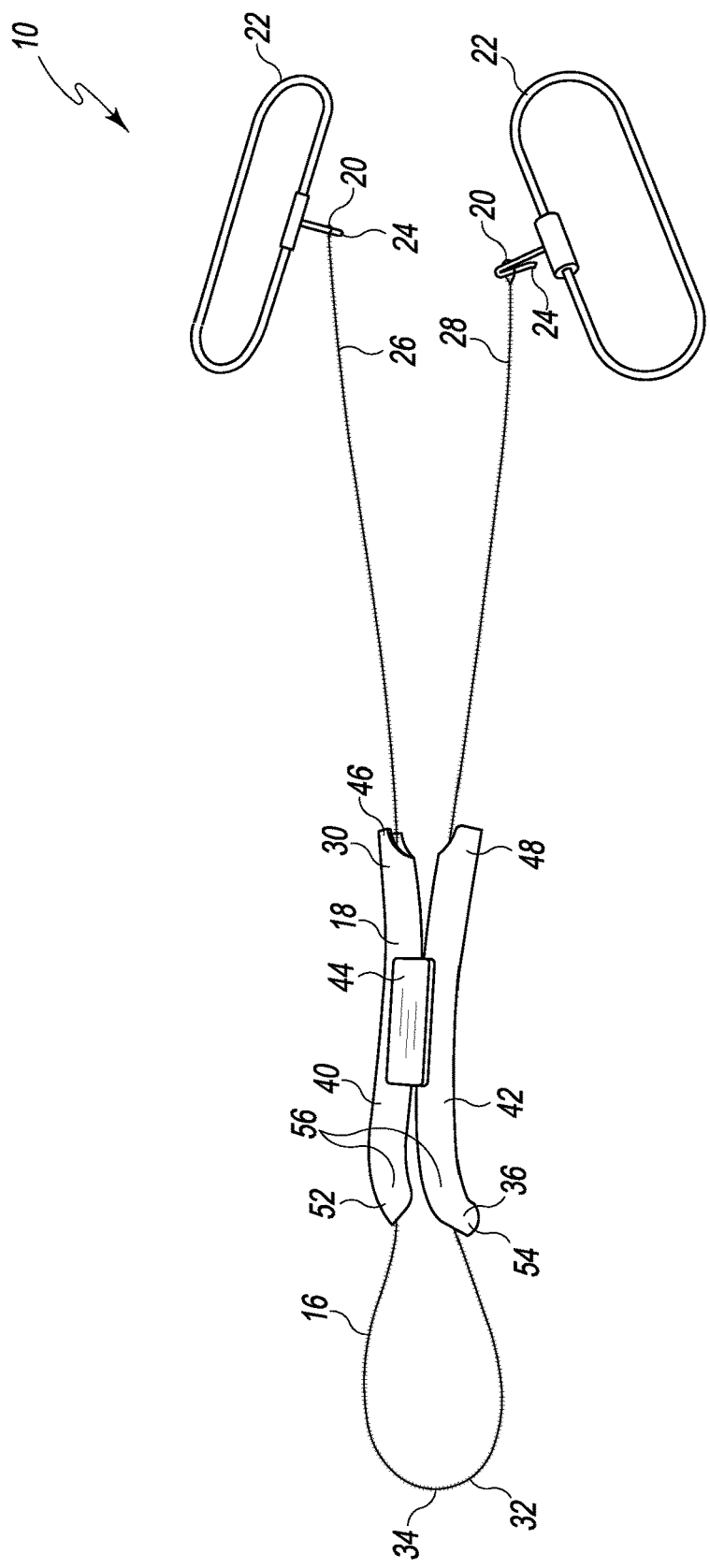
FIG. 1 is a perspective view of an orthopaedic surgical saw assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 2:
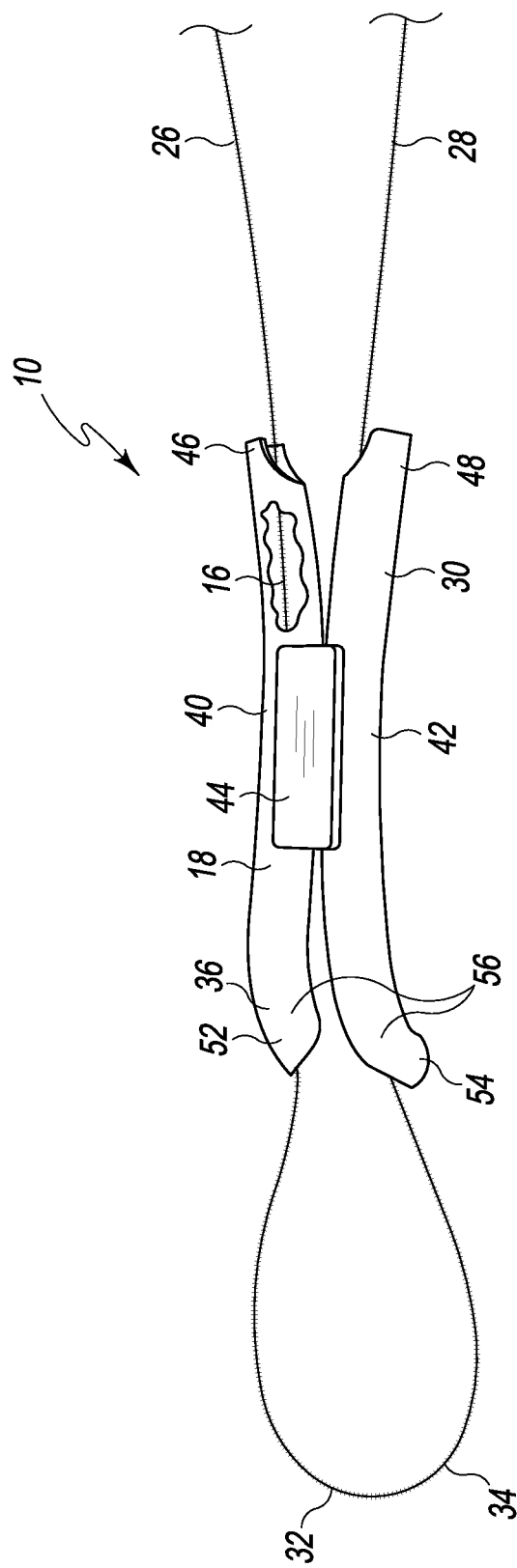
FIG. 2 is a perspective view of the dual-lumen cannula of the saw assembly of FIG. 1; note that a portion of the cannula has been cutaway for clarity of description.
Figure 3:
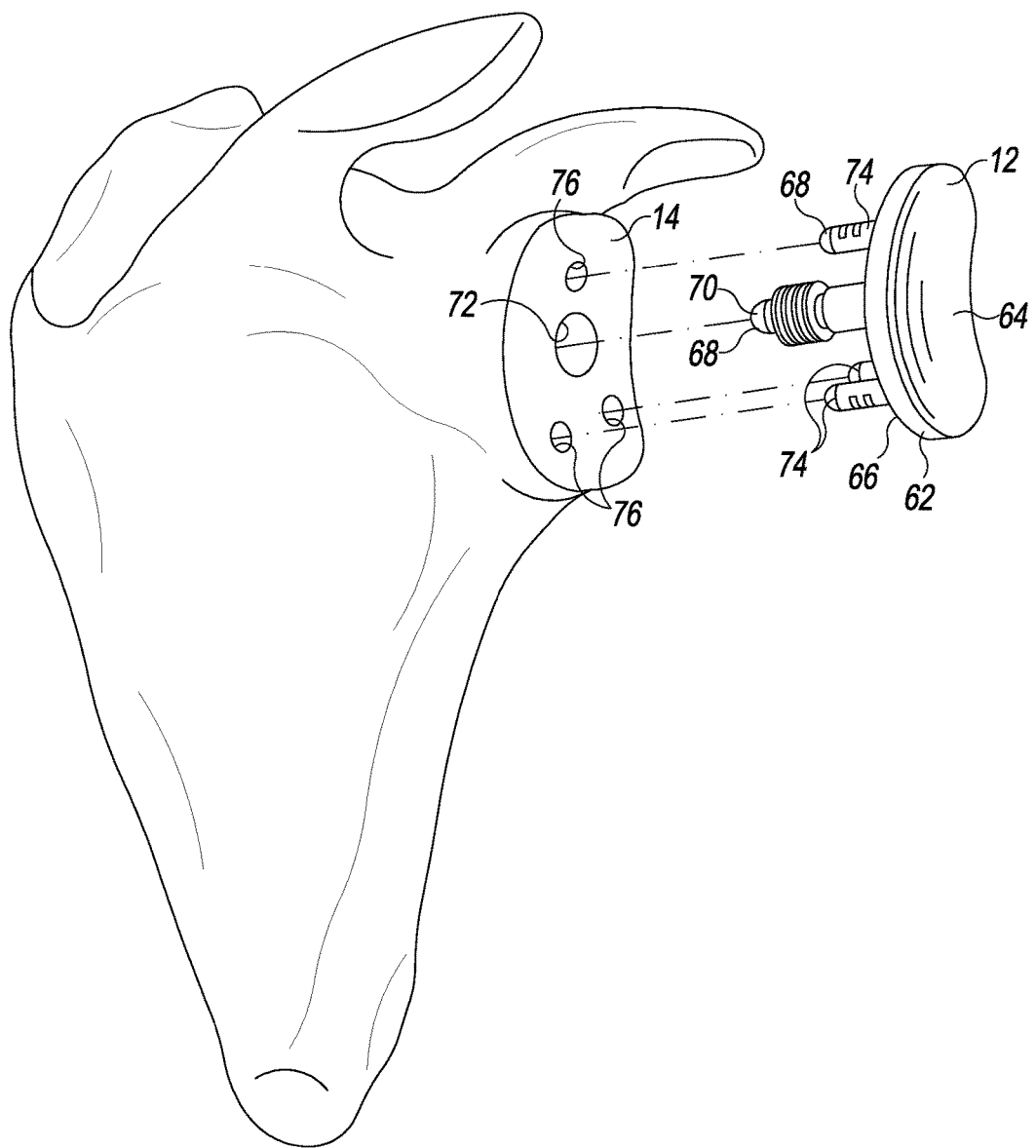
FIG. 3 is an exploded perspective view showing a glenoid component implanted in the glenoid of a patient during a primary orthopaedic surgical procedure.

Referring now to FIGS. 1 and 2, there is shown an orthopaedic surgical instrument 10 for removing an implanted glenoid component 12 from the glenoid 14 of a patient (see also FIG. 3). The surgical instrument 10 is embodied as a surgical saw assembly and, in the illustrative embodiment described herein, includes a flexible wire saw 16 and a protective cannula 18. The flexible wire saw 16 is embodied as a braided metallic cutting wire having a loop 20 formed in each of its ends. A handle 22 is secured to each end of the flexible wire saw 16 by inserting the handle's hook 24 into the loop 20. A surgeon grasps each handle to reciprocate the flexible wire saw 16 during its use in an orthopaedic surgical procedure. In the illustrative embodiment described herein, the flexible wire saw 16 is embodied as a commercially-available Gigli saw.

As can be seen in FIGS. 1 and 2, the flexible wire saw 16 is positioned in the protective cannula 18 such that both ends 26, 28 of the flexible wire saw 16 extend out of one end 30 of the protective cannula 18, with a middle section 32 of the flexible wire saw 16 forming a loop 34 that extends out of the other end 36 of the protective cannula 18. In the illustrative embodiment described herein, the protective cannula 18 is embodied as a dual-lumen cannula. As such, it is embodied as a pair of separate cannulae 40, 42 secured to one another by a connecting plate 44. In such an arrangement, one end 26 of the flexible wire saw 16 extends out of an end 46 of the cannula 40, with the other end 28 of the flexible wire saw 16 extending out of an end 48 of the cannula 42. The loop 34 formed from the middle section 32 of the flexible wire saw 16 extends between the respective opposite ends 52, 54 of the cannulae 40, 42.

Each of the cannulae 40, 42 has an elbow 56 formed near its respective distal end 52, 54. Such a shape facilitates proper positioning of the loop 34 formed from the middle section 32 of the flexible wire saw 16 during a cutting procedure.

Positioning the flexible wire saw 16 in the protective cannula 18 protects the patient's surrounding tissue during an orthopaedic procedure. Specifically, the protective cannula 18 prevents the moving flexible wire saw 16 from contacting the tissue surrounding the surgical site as the saw 16 is reciprocated back and forth within the surgical site. Moreover, the protective cannula 18 prevents the flexible wire saw 16 from slipping as it is operated.

Figure 4:
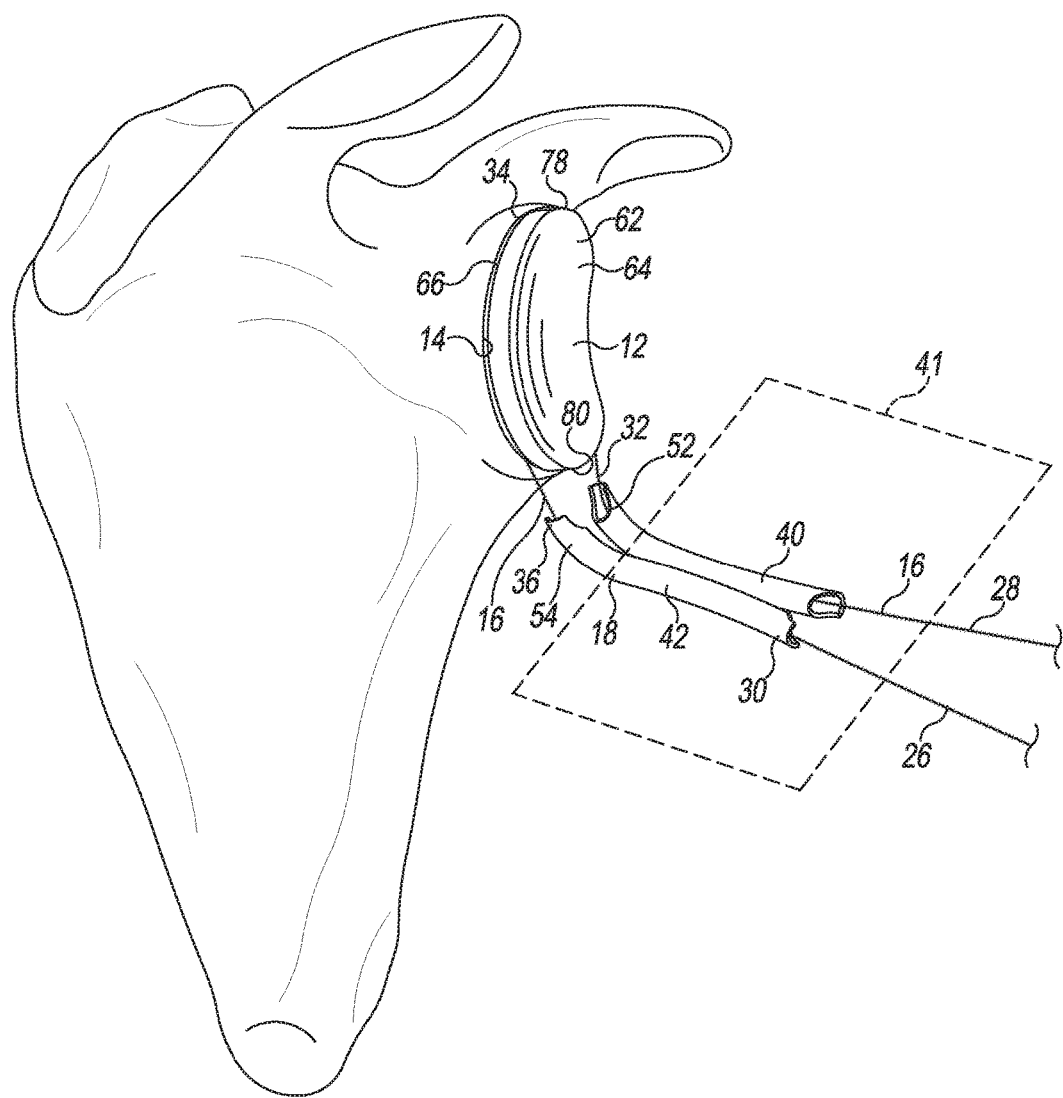
FIG. 4 is a perspective view showing the flexible wire saw of the saw assembly of FIG. 1 looped over the glenoid component during a revision surgical procedure to remove the glenoid component.
Figure 5:
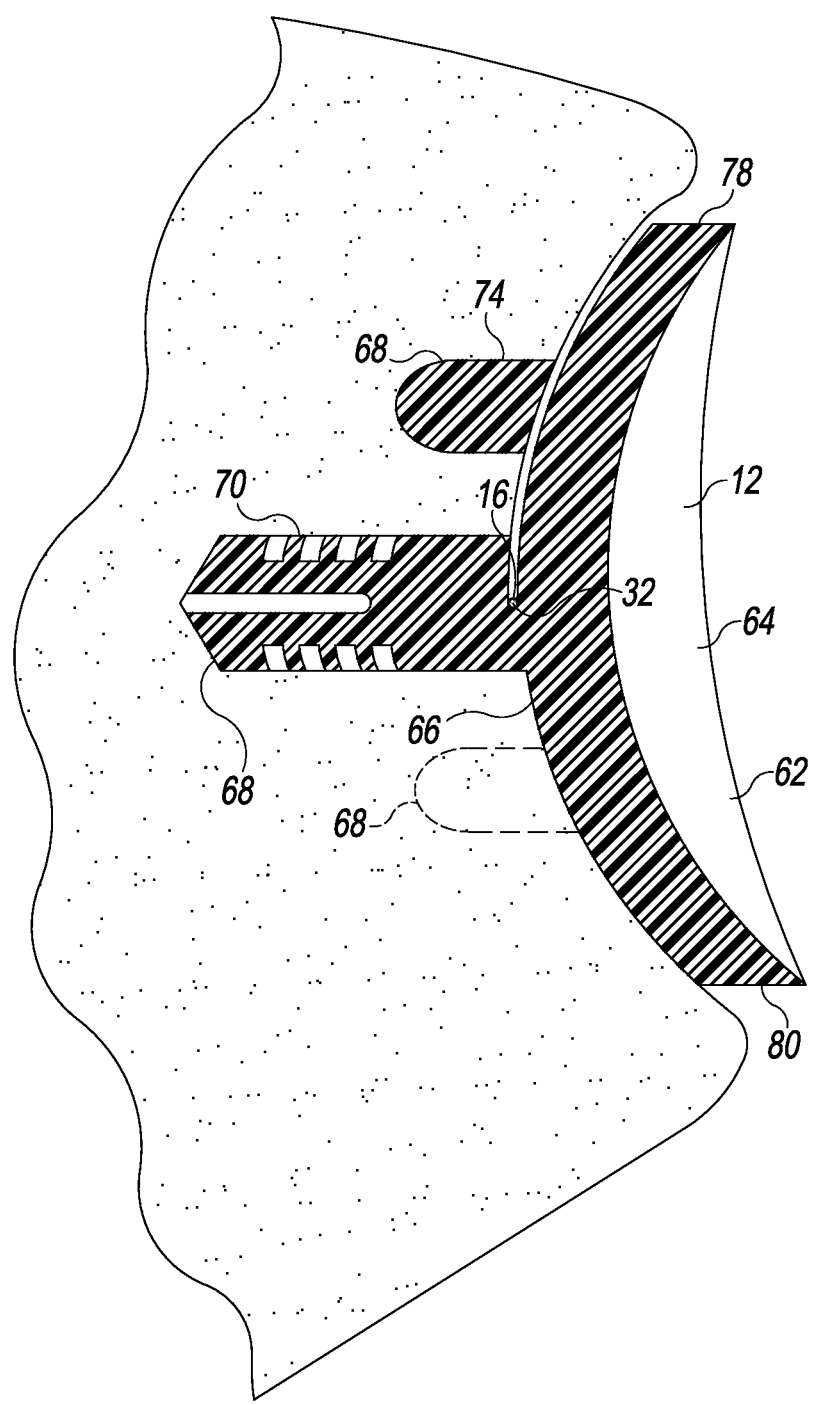
FIG. 5 is a fragmentary cross section view showing the flexible wire saw of the saw assembly of FIG. 1 being advanced through the anchors of the glenoid component.
Figure 6:
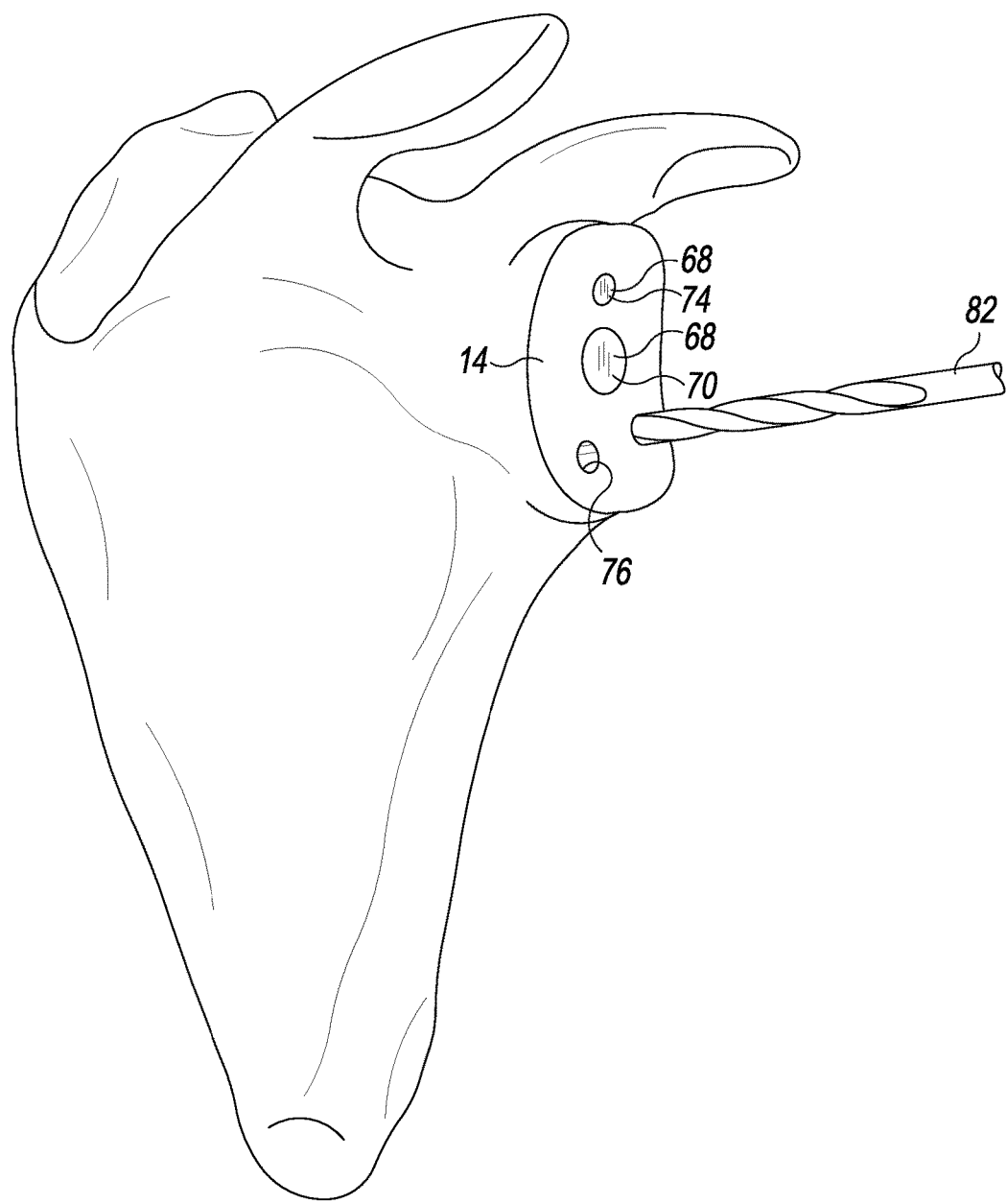
FIG. 6 is a perspective view showing a drill being used to drill out the anchors of the glenoid component after its platform has been removed with the saw assembly of FIG. 1.

Referring now to FIGS. 4-6, there is shown a revision surgical procedure in which the surgical saw assembly 10 is used to surgically remove a previously implanted glenoid component 12 from the glenoid 14 of a patient. As can be seen in FIG. 3, in a previous primary procedure, the glenoid component 12 is implanted in the patient's glenoid 14. A typical glenoid component 12 includes a platform 62 having a concave lateral surface 64 that provides a smooth bearing surface upon which a natural or prosthetic humeral head articulates. The platform 62 also has a convex medial surface 66 that is opposite its concave lateral surface 64.

The glenoid component 12 also includes a number of anchors 68 extending perpendicularly from the medial surface 66 of the glenoid component 12. For example, as shown in FIG. 3, the component's anchors 68 may take the form of a finned central peg 70 that is inserted into a hole 72 drilled or otherwise formed in the patient's glenoid 14 during the previous surgical procedure. The glenoid component's anchors 68 may also include a plurality of stabilizing pegs 74 that are received into a number of corresponding holes 76 drilled or otherwise formed in the glenoid 14 of the patient's scapula during the previous surgical procedure. Although the anchors 68 of the glenoid component 12 have herein been described as pegs, other types of anchors are commonly used in the design of glenoid components. For example, the glenoid component's anchors 68 may be embodied as keels, fins, posts, or any other type of anchor.

Typically, the glenoid component 12 is embodied as a monolithic molded component. That is, the platform 62 and the anchors 68 are integrally molded using a polymer such as polyethylene. One example of a commonly-used polyethylene is ultrahigh molecular weight polyethylene (UHMWPE).

During a revision surgery, it may be necessary to remove the previously implanted glenoid component 12 from the patient's glenoid 14. As shown in FIGS. 4-6, the surgical saw assembly 10 may used to surgically remove a previously implanted glenoid component 12 without leaving a large void in the patient's glenoid 14. To do so, the patient's soft tissue is dissected and retracted to allow access to the glenoid 14. Full (i.e., 360°) exposure of the bony glenoid is typically achieved.

As shown in FIG. 4, a plane 41 extends through each cannula 40, 42 of the protective dual-lumen cannula 18. The flexible wire saw 16 extends through the dual-lumen cannula 18 in a first orientation that is planar to the plane 41. The flexible wire saw 16 forms a loop 34 that extends outwardly from the distal ends 52, 54 of each elbow 56 in a second orientation that is angled out of the plane 41. The distal end 36 of the protective cannula 18 is then inserted into the surgical site formed by the dissected and retracted soft tissue. The surgeon then positions the flexible wire saw behind the platform 62 of the implanted glenoid component 12. In particular, the surgeon slips the loop 34 formed by the middle section 32 of the flexible wire saw 16 between the convex medial surface 66 of the glenoid component's platform 62 and the glenoid 14 of the patient's scapula. In the illustrative embodiment described herein, the surgeon slips the loop 34 formed by the middle section 32 of the flexible wire saw 16 behind the superior-most edge 78 of the glenoid component's platform 62.

If not already installed, the surgeon then secures a handle 22 to each end of the flexible wire saw 16 by inserting the handles hook 24 into the loops 20 formed on the ends 26, 28 of the saw 16. The surgeon then grasps a handle 22 with each hand and reciprocates or otherwise pulls the flexible wire saw 16 back and forth. The surgeon also applies downward pressure on the flexible wire saw 16 so that it advances inferiorly. As the flexible wire saw 16 is advanced inferiorly away from the superior-most edge 78 of the glenoid component's platform 62 in the direction toward its inferior-most edge 80, the reciprocating motion of the saw 16 abrades the polymer of the platform 62 and any ingrowth or adhesive material that may be present at the interface of the convex medial surface 66 of the glenoid component's platform 62 and the glenoid 14 of the patient's scapula (see FIG. 5).

As the flexible wire saw 16 is inferiorly advanced with such reciprocating motion, it encounters and cuts through the polymer anchors 68 of the implanted glenoid component 12. For example, in the illustration of FIG. 5, the flexible wire saw 16 has cut through one of the glenoid component's stabilizing pegs 74 and is partially through its finned central peg 70.

The surgeon continues to inferiorly advance the flexible wire saw 16 with reciprocating motion until the saw 16 exits from behind the glenoid component's platform 62. Specifically, the surgeon continues to reciprocate the flexible wire saw 16 until it passes beyond the inferior-most edge 80 of the glenoid component's platform 62. At that point, each of the glenoid component's anchors 68 have been cut through. The surgeon may then lift away the freed platform 62 of the glenoid component 12 from the patient's glenoid 14. As can be seen in FIG. 6, the newly cut anchors 68 (e.g., the finned central peg 70 and the stabilizing pegs 74) remain in the bone of the glenoid 14 once the platform of the glenoid component 12 has been removed.

As shown in FIG. 6, the anchors 68 may then be removed from the bone of the glenoid 14 to complete the removal of the glenoid component 12. For example, each of the stabilizing pegs 74 may be removed by selecting a drill bit 82 having the same diameter as the bit that was used to drill the holes 76 in the glenoid 14 of the patient's scapula during the previous surgical procedure (i.e., the primary procedure in which the glenoid component 12 was originally implanted). Such a similarly-sized drill bit 82 may then be used by the surgeon to drill the stabilizing pegs 74 out of the bone. The finned central peg 70 may likewise be removed by use of drill bit (not shown) having the same diameter as the bit that was used to drill the hole 72 during the previous surgical procedure.

Once the anchors 68 (e.g., the finned central peg 70 and the stabilizing pegs 74) have been removed, the surgeon may then perform the remainder of the revision surgical procedure, including the implantation of a revision glenoid component (not shown) into the patient's glenoid 14.

It should be appreciated that although the cutting procedure is herein described as advancing inferiorly away from the superior-most edge 78 of the glenoid component's platform 62 in the direction toward its inferior-most edge 80, other techniques may also be used. For example, the flexible wire saw 16 may be advanced superiorly, medially, laterally, or some combination thereof.

Figure 7:
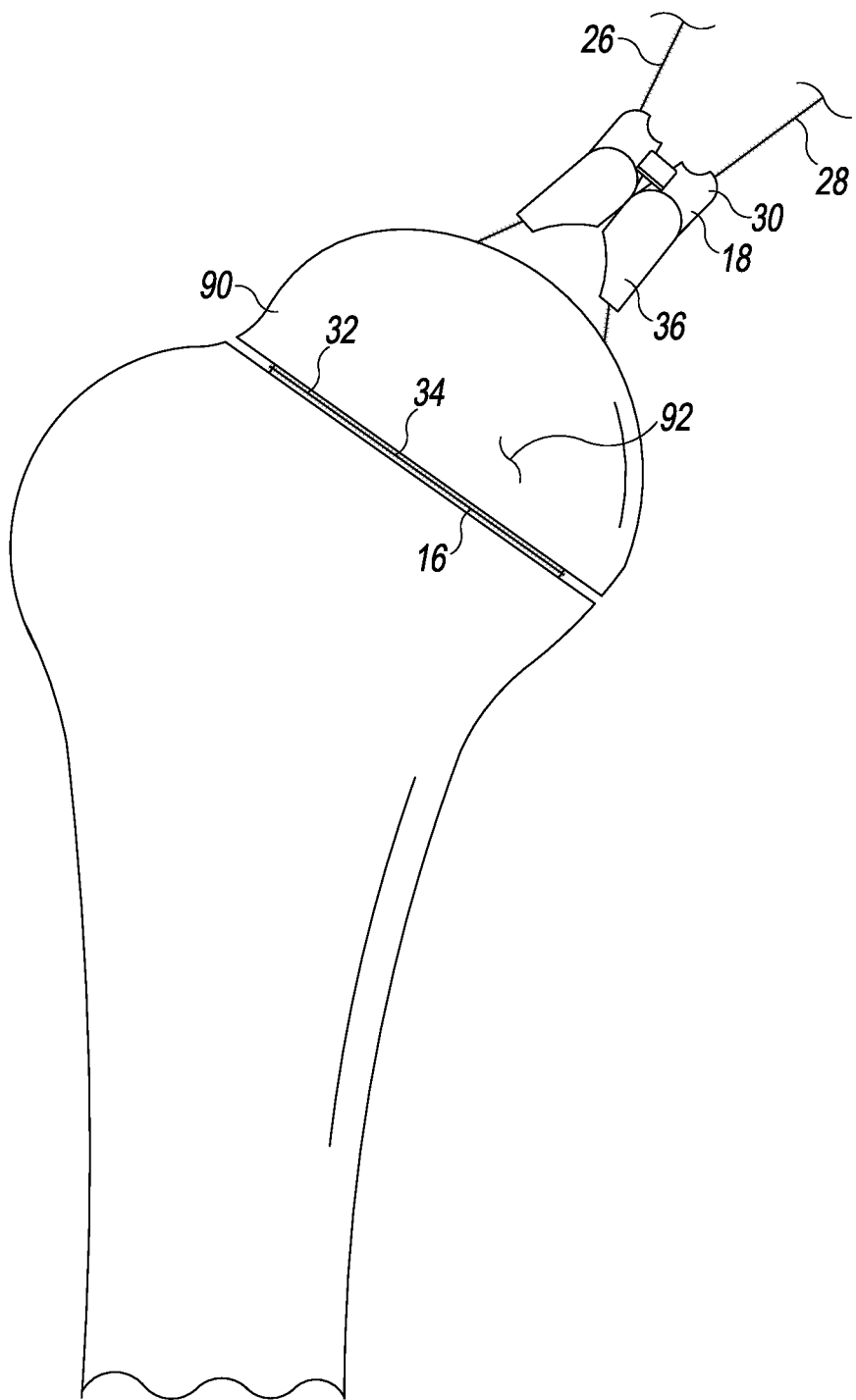
FIG. 7 is a perspective view showing the saw assembly of FIG. 1 being used to resect the natural humeral head of a patient.
Figure 8:
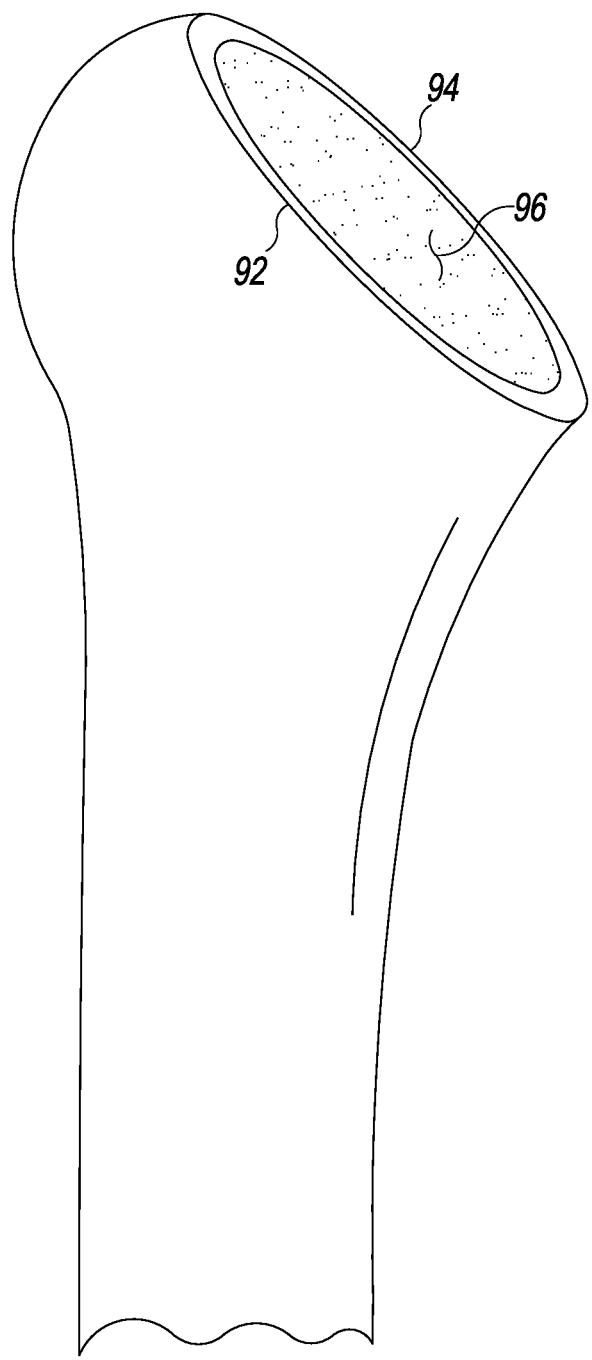
FIG. 8 is a view similar to FIG. 7, but showing the humeral head of the patient after it has been resected by use of the saw assembly of FIG. 1.

Turning now to FIGS. 7 and 8, there is shown a surgical procedure in which the surgical saw assembly 10 is used to surgically resect the natural humeral head 90 of a patient. Such resection of the humeral head is performed in shoulder arthroplasty procedures when it is necessary to replace the patient's natural humeral head 90 with a prosthetic head.

In the preliminary steps of the surgical procedure, the patient's soft tissue is dissected and retracted to allow access to the patient's humeral head 90. Full (i.e., 360°) exposure of the humeral head 90 is typically achieved. As can be seen in FIG. 7, the distal end 36 of the protective cannula 18 is then inserted into the surgical site formed by the dissected and retracted soft tissue. The surgeon then positions the flexible wire saw 16 in contact with the patient's humeral head 90. In particular, the surgeon slips the loop 34 formed by the middle section 32 of the flexible wire saw 16 around the humeral head 90 such that the inside of the loop 34 contacts the humeral head 90. In the illustrative embodiment described herein, the surgeon slips the loop 34 formed by the middle section 32 of the flexible wire saw 16 around the humeral head such that the inside surface of the loop 34 is in contact with the posterior surface 92 of the humeral head 90.

If not already installed, the surgeon then secures a handle 22 to each end of the flexible wire saw 16 by inserting the handles hook 24 into the loops 20 formed on the ends 26, 28 of the saw 16. The surgeon then grasps a handle 22 with each hand and reciprocates or otherwise pulls the flexible wire saw 16 back and forth. The surgeon also applies pressure on the flexible wire saw 16 so that it advances anteriorly. As the flexible wire saw 16 is advanced anteriorly away from the posterior surface 92 of the humeral head in the direction toward its anterior surface 94, the reciprocating motion of the saw 16 abrades the bone tissue of the humeral head 90.

The surgeon continues to anteriorly advance the flexible wire saw 16 with reciprocating motion until the saw 16 exits the bone. Specifically, the surgeon continues to reciprocate the flexible wire saw 16 until it passes beyond the anterior surface 94 of the humeral head 90. At that point, the surgeon may then lift away the resected portion of the patient's humeral head 90. As can be seen in FIG. 8, the surgically prepared surface 96 of the humeral head 90 is substantially planar.

Once the substantially planar surgically prepared surface 96 of the humeral head 90 has been created, the surgeon may then perform the remainder of the surgical procedure, including the implantation of a humeral stem component (not shown) into the intramedullary canal of the patient's humerus.

It should be appreciated that although the humeral cutting procedure is herein described as advancing posteriorly away from the anterior surface 94 of the humeral head 90 in the direction toward its anterior surface 94, other techniques may also be used. For example, the flexible wire saw 16 may be advanced posteriorly, medially, laterally, or some combination thereof.

It should also be appreciated that other embodiments of the protective cannula 18 may be used in the humeral cutting procedure described in regard to FIGS. 7 and 8. For example, the protective cannula 18 may be embodied as a cannulated ring having the flexible wire saw 16 captured therein. Such a cannulated ring provides support for the flexible wire saw 16, while also allowing the surgeon to size the humeral head.

Although the various cutting procedures disclosed herein are illustratively described as manual cutting techniques in which the surgeon manually reciprocates the flexible wire saw 16, other techniques are also contemplated for use. In particular, the flexible wire saw 16, with or without modification thereto, may be used in conjunction with a powered surgical tool. In such a case, the powered surgical tool supplies the motive power to move the wire saw 16 in lieu of the surgeon's manual motion.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A surgical instrument for removing an implanted glenoid component from the glenoid of a patient, comprising:
   a protective dual-lumen cannula having a first cannula and a second cannula positioned adjacent to the first cannula, each of the first cannula and the second cannula having a proximal end, a distal end, and an elbow positioned adjacent to each of the distal ends, and
   a flexible wire saw having a first wire section including a first end, a second section including a second end opposite the first end, and a middle section positioned between the first end and the second end, wherein each of the elbows is configured to redirect the wire saw from a first orientation to a second orientation for cutting through the glenoid component, wherein, in the first orientation, the first wire section and the second wire section of the wire saw extend substantially coplanar to a plane defined by the first cannula and the second cannula of the protective dual-lumen cannula, and, in the second orientation, the middle section of the wire saw is angled out of the plane, and
   wherein the first end of the flexible wire saw extends out of the proximal end of the first cannula, the second end of the flexible wire saw extends out of the proximal end of the second cannula, and the middle section of the flexible wire saw forms a loop that extends outwardly in the second orientation from the distal end and the elbow of the first cannula and outwardly in the second orientation from the distal end and the elbow of the second cannula such that the middle section of the flexible wire saw is exposed to cut the glenoid component.

2. The surgical instrument of claim 1, wherein the flexible wire saw comprises a Gigli saw.

3. The surgical instrument of claim 1, wherein the protective cannula is metallic.

4. The surgical instrument of claim 1, wherein the protective cannula is polymeric.

* * * * *